United States Patent
Mullani

(10) Patent No.: US 10,244,944 B2
(45) Date of Patent: Apr. 2, 2019

(54) VEIN TRANSILLUMINATION DEVICE USING ORANGE AND RED LIGHT WITH A WHITE EXAM LIGHT

(71) Applicant: Translite, LLC, Sugar Land, TX (US)

(72) Inventor: Nizar Mullani, Sugar Land, TX (US)

(73) Assignee: Translite, LLC, Sugar Land, TX (US)

( * ) Notice: Subject to any disclaimer, the term of this patent is extended or adjusted under 35 U.S.C. 154(b) by 58 days.

(21) Appl. No.: 14/840,661

(22) Filed: Aug. 31, 2015

(65) Prior Publication Data

US 2016/0242649 A1    Aug. 25, 2016

Related U.S. Application Data

(60) Provisional application No. 62/118,706, filed on Feb. 20, 2015.

(51) Int. Cl.
*A61B 5/00* (2006.01)

(52) U.S. Cl.
CPC .......... *A61B 5/0059* (2013.01); *A61B 5/0077* (2013.01); *A61B 5/489* (2013.01); *A61B 5/7475* (2013.01); *A61B 2560/0214* (2013.01); *A61B 2560/0406* (2013.01); *A61B 2560/0425* (2013.01); *A61B 2562/0238* (2013.01)

(58) Field of Classification Search
CPC ..... A61B 5/0059; A61B 5/489; A61B 5/0077; A61B 5/7475; A61B 2560/0406; A61B 2560/0214; A61B 2560/0238; A61B 2560/0425
USPC .......... 362/202, 277, 280, 319, 351
See application file for complete search history.

(56) References Cited

U.S. PATENT DOCUMENTS

| | | | |
|---|---|---|---|
| 4,651,743 A | 3/1987 | Stoller | |
| 5,957,917 A | 9/1999 | Doiron et al. | |
| 6,923,762 B1 | 8/2005 | Creaghan, Jr. | |
| 7,167,243 B2 | 1/2007 | Mullani | |
| 7,874,698 B2 | 1/2011 | Mullani | |
| 2004/0174525 A1* | 9/2004 | Mullani | A61B 5/0059 356/369 |
| 2004/0201846 A1* | 10/2004 | Mullani | A61B 5/0059 356/369 |
| 2005/0254234 A1* | 11/2005 | Wang | F21L 4/027 362/184 |
| 2006/0132774 A1 | 6/2006 | Mullani | |
| 2006/0250798 A1* | 11/2006 | Herold | F21L 4/00 362/280 |
| 2008/0015663 A1* | 1/2008 | Mullani | A61B 5/0059 607/90 |

(Continued)

*Primary Examiner* — Peter Luong
(74) *Attorney, Agent, or Firm* — Welsh, Flaxman & Gitler, LLC

(57) ABSTRACT

An illumination device that has an orange light, with LEDs having a wavelength in the range of 580-620 nm, and/or a red light with LEDs having a wavelength of light in the range of 620-650 nm for side-transillumination of the veins. Orange light has been found to be beneficial for transillumination of superficial veins, while red light has been found to be beneficial for transillumination of deeper veins. In addition, the device has white light which is used for illumination of the surface of the skin. The illumination device contains a manual or automatic switch or switching mechanism that allows the user to easily switch between the orange light/red light and the white exam light by simply pressing a button or moving the device.

4 Claims, 1 Drawing Sheet

(56) References Cited

U.S. PATENT DOCUMENTS

2010/0256455 A1    10/2010   Hsia et al.
2012/0101342 A1    4/2012   Duffy et al.
2015/0036311 A1    2/2015   Mullani

* cited by examiner

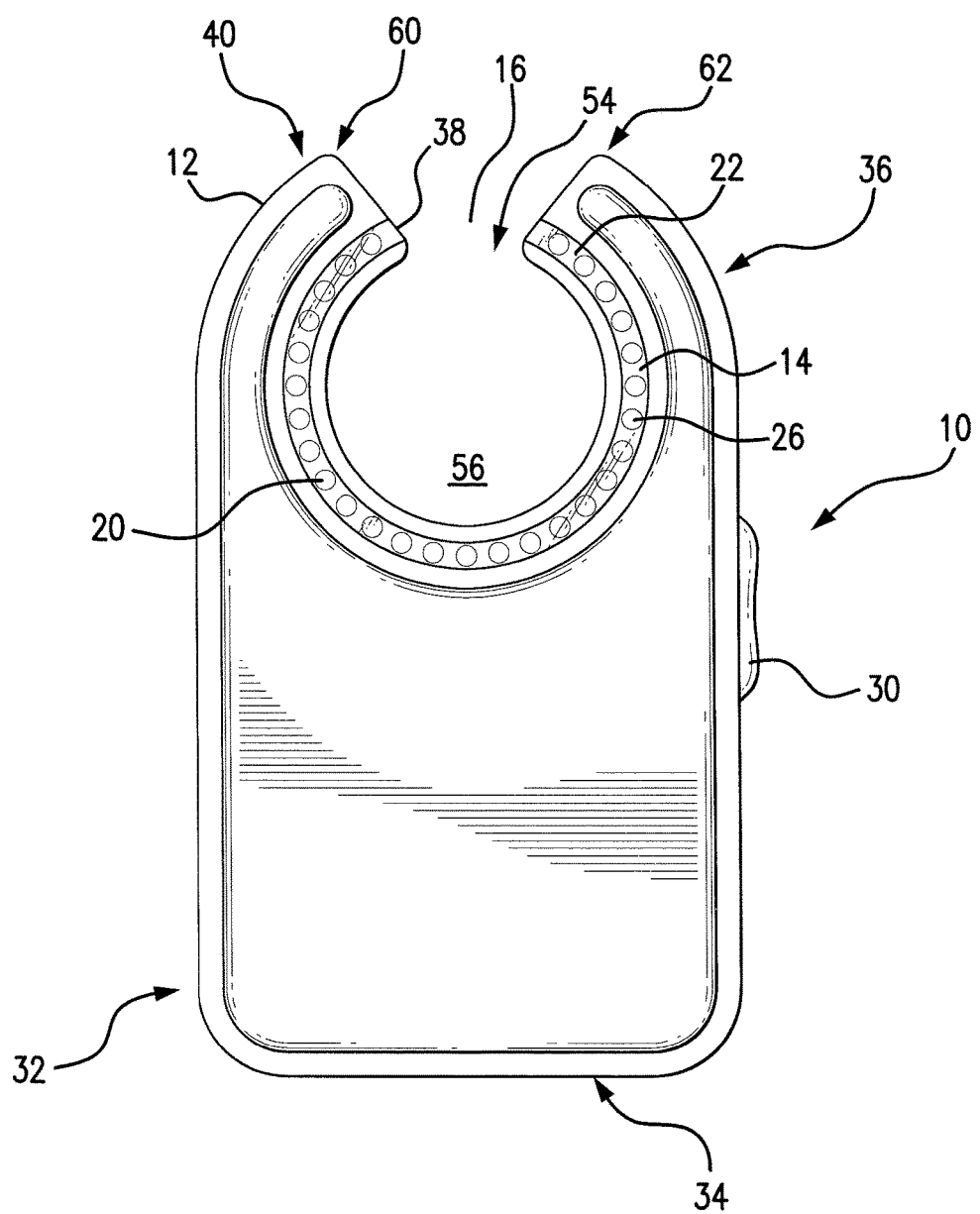

VEIN TRANSILLUMINATION DEVICE USING ORANGE AND RED LIGHT WITH A WHITE EXAM LIGHT

CROSS REFERENCE TO RELATED APPLICATION

This application claims the benefit of U.S. Provisional Patent Application Ser. No. 62/118,706, entitled "VEIN TRANSILLUMINATION DEVICE USING ORANGE AND RED LIGHT WITH A WHITE EXAM LIGHT," filed Feb. 20, 2015.

BACKGROUND OF THE INVENTION

Transillumination entails shining of a light through a body cavity or organ for diagnostic purposes. Typically, transillumination is performed in a room where the lights have been dimmed or turned off to facilitate the viewing of the part being studied. A bright light is pointed at the cavity or organ and due to the slight translucence of the part under consideration, some of the light passes through the part or organ. This test is often performed on newborns or infants with hydrocephalus or males suspected of having hydrocele. In addition, transillumination is used for tests performed on breast tissue to detect lesions and/or cysts. In newborns, the test is used to transilluminate the chest cavity if pneumothorax is suspected. Only in newborns is transillumination of the chest possible. Transillumination is painless and quickly performed with inexpensive equipment.

Transilluminators use color to facilitate the viewing of the tissue organ under study. U.S. Pat. No. 4,651,743 issued to Stoller discloses a transillumination device using red light. In addition, U.S. Pat. No. 5,957,917 issued to Doiron et al discloses that red light is particularly useful for performing transillumination of tissue for diagnostic purposes. Further, U.S. Pat. No. 7,874,698 issued to Mullani relates to transillumination having an orange color light. These devices use colored light at a specified wavelength to illuminate veins that are positioned below a skin surface. Typically, the vein transilluminator uses a side-transillumination method where light shines into the skin from the top and at an angle to the skin so that the light is focused approximately 2 to 4 cm below the skin. The annulus of focused light behaves like a virtual light source under the skin and transilluminates an area of the skin inside the circle of light.

When it is the desire of the user to examine the surface of the skin, a separate device that uses white light of a particular wavelength is utilized. In order to do an exam of the skin of a patient, a separate white light source is used to shine light on the patient thus requiring two devices, one for transillumination the vein and a second for examination of the patient.

It is therefore an object of the invention to provide a device that combines two separate distinct functions, namely, a vein transillumination light device and a white examination light device, thus eliminating the need to have two separate light sources.

It is another object of the invention to provide a simplified illumination device that can easily switch between two devices.

It is another object of the invention to have an illumination device with colored lights for transillumination of superficial veins and deeper veins and white light LEDs for illumination of the skin of the patient.

These and other objects of the invention will become apparent to one of ordinary skill in the art after reviewing the disclosure of the invention.

SUMMARY OF THE INVENTION

The illumination device has an orange light, with LEDS having a wavelength in the range of 580-620 nm, and/or a red light with LEDs having a wavelength of light in the range of 620-650 nm for side-transillumination of the veins. Orange light has been found to be beneficial for transillumination of superficial veins, while red light has been found to be beneficial for transillumination of deeper veins. In addition, the device has white light which is used for illumination of the surface of the skin. The illumination device contains a manual or automatic switch or switching mechanism that allows the user to easily switch between the orange light/red light and the white exam light by simply pressing a button or moving the device. One single device contains both light sources and LEDs, each having different colors which may be used for different purposes. The light sources may be fiber optic or LED.

BRIEF DESCRIPTION OF THE DRAWINGS

FIG. 1 is a bottom view of an illumination device.

DETAILED DESCRIPTION OF THE INVENTION

The illumination device depicted in FIG. 1 has a housing 12 having a handle portion 32 at a first end 34 thereof and an illumination portion 36 with a light generating source 38 at a second end 40 thereof.

Referring to the handle portion 32, it is substantially rectangular shaped, although it is appreciated that it may take a variety of shapes as the preferences of different users might dictate. Regardless of its shape, the handle portion 32 is shaped and dimensioned to allow a user to securely grip the handle portion 32.

The housing 12 also contains a power source for the light generating source 38. In accordance with a preferred embodiment, the power source is substantially contained with the handle portion 32 and is associated with at least one user controlled switch 30 allowing for actuation of the two light generating sources 38 in controlled manner for the selective examination of a user's skin or veins.

As for the illumination portion 36 of the housing 12, it includes a substantially circular shaped area of illumination 14. The illumination portion 36 may be thought of as including a proximal end that merges into the handle portion 32 and a distal end at which the circular shaped area of illumination 14 is positioned such that the circular shaped area of illumination 14 extends from the front edge of the housing 12 at the distal end of the illumination portion 36 to form a viewing area.

More particularly, the circular shaped area of illumination 14 is defined by a circular recess 54 formed at the distal end of the illumination portion 36 (at the second end 40 of the housing 12). The recess 54 includes a substantially circular central space 56 and an opening 58 extending from the substantially circular central space 56 to the front edge 54 of the housing 12. With this in mind, the recess 54 creates opposed arms 60, 62 along the housing 12 that extend to enclose a space of approximately 270 degrees. Each of the arms 60, 62 tapers inwardly as they extend from the upper surface of the housing 12 to the lower surface of the housing 12, focusing a user's eye upon the center of the recess 54 when the user looks downwardly upon the upper surface of the housing 12 toward light being transmitted away from the lower surface of the housing 12.

As briefly discussed above, the circular shaped area of illumination 14 includes a series of lights, of desired frequencies projected from the lower surface of the housing for either illumination of the skin, as desired, in accordance with the present invention, or transillumination of a vein. The light generating source 38 is formed in the lower surface of the housing 12 in the illumination portion 36. The light generating source 38 is shaped and dimensioned to encircle the substantially circular central space 56 of the recess 54. Accordingly, the light generating source 38 is of a semicircular shape extending about an arc of approximately 270 degrees, and follows the edge of the circular central space 56 along the lower surface of the housing 12. The light generating source 38 is focused to project light of predetermined frequencies toward the center of the substantially circular central space.

The light generating source 38 is composed of two distinct light sources 20, 22. The first light source 20 generates orange and/or red light having a wavelength enabling vein transillumination. In accordance with a preferred embodiment, the light is orange and has a wavelength between 580 and 620 nm. It is appreciated, the use of an orange light with a wavelength between 580 and 620 nm allows for enhanced imaging of superficial veins, while red light with frequencies between 620 and 650 nm optimizes viewing of deeper veins through darker skin. The illumination device may have a light source which can transmit both orange and/or red light which enables side transillumination of veins of different depths, as desired. Orange light has higher absorption in venous blood than red light whereas red light penetrates deeper in darker, pigmented skin, thus allowing better vein illumination in dark skinned patients.

The second light source 22 generates white light that enables skin surface illumination for direct examination of the patient's skin. As those skilled in the art will appreciate, white light is a combination of lights of different wavelengths.

The first and second light sources 20, 22 are preferably composed of alternating LEDs that run along the substantially circular shaped area of illumination 14 so as to project light from the lower surface 44 of the housing 12 toward a patient being examined. The illumination device is placed near the patient's skin for vein or skin surface imaging, as desired. Other applications of transillumination devices are well known.

The first light source 20 is, in one preferred embodiment, composed of a series of sixteen LEDs comprising twelve orange-colored LEDs positioned for emitting orange light outwardly from the lower surface 44 of the housing 12 and four red-colored LEDs positioned for emitting red light outwardly from the lower surface of the housing 12, 20a-20p. Intermixed with the series of sixteen orange and red-colored LEDs 20a-20p, making up the first light source 20, are the white-colored LEDs making up the second distinct light source 22. The second light source 22 is composed of a series of 8 white-colored LEDs 22a-22h symmetrically dispersed amongst the sixteen orange-colored LEDs 20a-20p, in this preferred embodiment. In accordance with a preferred embodiment, the pattern extending about the substantially circular shaped area of illumination 14, begins at a position of approximately 10 o'clock as shown in FIG. 1 and extends in a counterclockwise direction. The pattern includes the following sequence of LEDs, two orange-colored LEDs 20a, 20b, one white-colored LED 22a, one red and one orange-colored LED 21a, 20c, one white-colored LED 22b, one orange and one red-colored LED 20d, 21b, one white-colored LED 22c, two orange-colored LEDs 20e, 20f, two white-colored LEDs 22d, 22e, two orange-colored LEDs 20g, 20h, one white-colored LED 22f, one red and one orange-colored LED 21c, 20i, one white-colored LED 22g, one orange and one red-colored LED 20j, 21d, one white-colored LED 22h, followed by two orange-colored LEDs 20k, 20l. This pattern runs the length of the substantially shaped circular area of illumination 14.

In use, when the switch 30 is first depressed the first light source 20 is illuminated projecting orange light from the series of sixteen orange-colored LEDs 20a-20p for side transillumination of veins. In this mode, the user achieves transillumination by placing the lower surface 44 of the housing 12 directly upon the skin. In particular, the side-transillumination shines light into the skin from the top and at an angle to the skin so that the light is preferably focused approximately 2 to 4 cm below the skin. The annulus of focused light behaves like a virtual light source under the skin and transilluminates an area of the skin inside the circle of light.

When the device's switch 30 is pressed again, a second light source 22 is illuminated projecting white light from the series white-colored LEDs 22a-22h to simply examine the skin of a patient. In this mode, the lower surface 44 of the housing 12 is preferably positioned about 12 to 24 inches away from the skin allowing white light to illuminate the skin of a patient for examination.

When the device's switch 30 is pressed a third time, both the first and second light sources 20, 22 are illuminated. Finally, when the device's switch 30 is pressed a fourth time, both the first and second light sources 20, 22 are turned off. This enables the user to view the surface of the skin or side-illuminate a vein using a single device. The ability to have one device to view both the surface of a patient's skin and vein side-transillumination provides significant savings to the user, by enabling such to occur in one simple handheld device.

Further, there is provided a method of viewing both the surface of the skin of a patient and veins of a patient by using one compact device. The method includes the steps of using the device as described above to perform an examination without the examiner having to use a separate device and interrupt the examination.

Although the disclosed embodiment is manually controlled, it is contemplated an automatic sensor can be utilized such that when the unit is in touch with the skin, it will switch on the first light source 20 and when it is away from the skin, it will turn on the second light source.

While the invention has been described with reference to a preferred embodiment, variations and modifications would be apparent to one of ordinary skill in the art. Such variations and modifications are encompassed by the invention.

What is claimed is:

1. An illumination device comprising in combination:
a housing having a handle portion at a first end thereof and an illumination portion with an arc-shaped light generating source at a second end thereof, the housing also having a recess at the second end thereof, the recess being composed of a circular central space and an opening, and the arc-shaped light generating source encircles the circular central space of the recess,
a power source within the arc-shaped light generating source substantially contained with the handle portion has at least one user controlled switch on a side edge of the housing, allowing for actuation of the arc-shaped light generating source and switching between a type of illumination, either transillumination or surface illumination, in controlled manner for the selective examination of a user's skin or veins, the arc-shaped light generating source including a transillumination orange light composed of LEDs having a wavelength in the range of 580-620 nm, a red light composed of LEDs having a wavelength of light in the range of 620-650 nm for side-transillumination of the veins, and a white exam light composed of LEDs for illumination of the surface of the skin, the illumination portion includes a substantially semicircular shaped area of illumination shaped and dimensioned to encircle the substantially semicircular central area, the arc-shaped light generating source of the illumination portion extending about an arc of approximately 270 degrees and following an edge of the semicircular central area along a lower surface of the housing, and the arc-shaped light generating source includes the transillumination orange light composed of LEDs, the red light composed of LEDs for side-transillumination of the veins and the white exam light composed of LEDs that run along the substantially semicircular shaped area of illumination, wherein the at least one user controlled switch allowing for actuation of the arc-shaped light generating source of the illumination device further comprises a manual or automatic switch to switch between the orange light, the red light and the white exam light by simply pressing a button or moving the device and wherein a pattern of LEDs comprises a series of sixteen LEDs comprising twelve orange-colored LEDs positioned for emitting orange light outwardly from the lower surface of the housing and four red-colored LEDs positioned for emitting red light outwardly from the lower surface of the housing and intermixed with the series of sixteen LEDs are the white-colored LEDs composed of a series of eight white-colored LEDs symmetrically dispersed amongst the sixteen LEDs, wherein the twelve orange-colored LEDs and the four red-colored LEDs make up a first light source, and the white-colored LEDs make up a distinct second light source the second light source is composed of the eight white-colored LEDs symmetrically dispersed amongst the twelve orange-colored LEDs and four red-colored LEDs, whereby the pattern of LEDs extending about the substantially circular shaped area of illumination begins at a position of approximately 10 o'clock and extends in a counter-clockwise direction.

2. The illumination device as claimed in claim 1, wherein the handle portion is shaped and dimensioned to allow a user to securely grip the handle portion.

3. The illumination device as claimed in claim 1, wherein the substantially semicircular shaped area of illumination merges into the handle portion and the substantially circular shaped area of illumination extends from the front edge of the housing at a distal end of the illumination portion to form a viewing area.

4. The illumination device of claim 1, wherein the pattern of LEDs includes a sequence of LEDs comprising, two orange-colored LEDs, one white-colored LED, one red-colored LED and one orange-colored LED, one white-colored LED, one orange-colored LED and one red-colored LED, one white-colored LED, two orange-colored LEDs, two white-colored LEDs, two orange-colored LEDs, one white-colored LED, one red-colored LED and one orange-colored LED, one white-colored LED, one orange-colored LED and one red-colored LED, one white-colored LED, followed by two orange-colored LEDs running a length of the substantially shaped circular area of illumination.

* * * * *